US009061012B2

(12) United States Patent
Meyers et al.

(10) Patent No.: US 9,061,012 B2
(45) Date of Patent: Jun. 23, 2015

(54) USES OF DGAT1 INHIBITORS

(75) Inventors: Charles Meyers, Littleton, MA (US); Michael H. Serrano-Wu, Belmont, MA (US); Tom Thuren, Succasunna, NJ (US)

(73) Assignee: Novartis AG, Basel (CH)

( * ) Notice: Subject to any disclaimer, the term of this patent is extended or adjusted under 35 U.S.C. 154(b) by 111 days.

(21) Appl. No.: 13/637,372

(22) PCT Filed: Mar. 29, 2011

(86) PCT No.: PCT/US2011/030234
§ 371 (c)(1),
(2), (4) Date: Sep. 26, 2012

(87) PCT Pub. No.: WO2011/123401
PCT Pub. Date: Oct. 6, 2011

(65) Prior Publication Data
US 2013/0023495 A1  Jan. 24, 2013

Related U.S. Application Data

(60) Provisional application No. 61/318,814, filed on Mar. 30, 2010.

(51) Int. Cl.
*A61K 31/44* (2006.01)
*A61K 31/42* (2006.01)

(52) U.S. Cl.
CPC ..................................... *A61K 31/42* (2013.01)

(58) Field of Classification Search
USPC ....................................................... 514/332
See application file for complete search history.

(56) References Cited

U.S. PATENT DOCUMENTS

2009/0247534 A1*  10/2009  Serrano-Wu et al. .... 514/252.03

FOREIGN PATENT DOCUMENTS

WO  WO 2007/126957   11/2007
WO  WO 2009/040410    4/2009

OTHER PUBLICATIONS

Zhao, G. et al., J. Med. Chem. vol. 51 pp. 380-383. Published 2008.*
Santamarina-Fojo, S. Lipid Disorders vol. 27 pp. 551-567. Published 1998.*
Chait, A., et al. Advances in Internal Medicine. vol. 37 pp. 249-273. Published 1991.*
Zhao, G. et al., J. Med. Chem. vol. 51, pp. 380-383, published 2008.*
Santamarina-Fojo, S. Lipid Disorders vol. 27, pp. 551-567. Published 1998.*
Chait, A. et al. Advances in Internal Medicine vol. 37, pp. 249-273. Published 1991.*
Reagan Shaw, S. et al. FASEB J vol. 22, pp. 659-661. Published 2007.*
Zhao et al (J. Med. Chem., vol. 51, pp. 380-383, published 2008).*
Santamarina-Fojo et al (Lipid Disorders vol. 27, pp. 551-567, published 1998).*
Zhao et al., "Validation of Dlacylglycarolacyltransferase I as a novel target for the treatment of obesity and dyslipidemia using a potent and slective molecule inhibitor", Journal Medicinal Chemistry, vol. 51, pp. 380-383, 2008.
Chen Hubert C. et al: "Inhibition of triglyceride synthesis as a treatment strategy for obesity, lessons from DGAT1-deficient mice", Arteriosclerosis Thrombosis and Vascular Biology, vol. 25, pp. 482-486, Nov. 15, 2004.
Yen Chi-Liang Eric et al: "DGAT enzymes and triacylglerol biosynthesis", Journal of Lipid Research, vol. 49, pp. 2283-2301, Aug. 29, 2008.
Shi Yuguang et al: "Beyond triglyeride synthesis: the dynamic functional roles of MGAT and DGAT enzymes in energy metabolism", Am J Physiol Endocrinol Metab 297: E10-E18, Dec. 22, 2008.
Birch Alan M et al: "DGAT1 inhibitors as anti-obesity and anti-diabetic agents", Current Opinion in Drug Discovery & Development, 2010 vol. 13, No. 4, pp. 489-496.
Mero Niina et al: "Delayed clearance of postprandial large TG-rich particles in normolipidemic carriers of LPL Asn291 Ser gene variant", Journal of Lipid Research vol. 40(9), pp. 1663-1678, 1999.
King, Andrew J. et al: "Diacylglycerol acyltransferase 1 inhibition . . . ", The Journal of Pharmacology & Experimental Therapeutics, 330(2) : 526-531, May 26, 2009.

* cited by examiner

*Primary Examiner* — Paul Zarek
*Assistant Examiner* — George W Kosturko
(74) *Attorney, Agent, or Firm* — James L. Lynch (57) ABSTRACT

The present invention relates to the use of a DGAT1 inhibitor, or a pharmaceutically acceptable salt or ester thereof, for the prevention, delay of progression or treatment of a disease or condition which is selected from chylomicronemia syndrome, familial chylomicronemia syndrome and Type V hyperlipoproteinemia. The present invention further relates to the use of a pharmaceutical composition comprising a DGAT1 inhibitor, or a pharmaceutically acceptable salt or ester thereof, for the prevention, delay of progression or treatment of a disease or condition which is selected from chylomicronemia syndrome, familial chylomicronemia syndrome and Type V hyperlipoproteinemia.

5 Claims, 5 Drawing Sheets

Figure 1    Classification of Hypertriglyceridemia and Chylomicronemia

Figure 2: Effect of the compound 1 on an intralipid-induced plasma TG excursion in HF-STZ rats;

Figure 3: Effect of a DGAT1 inhibitor on plasma triglycerides in a model of impaired triglyceride clearance.

Figure 4   Effect of Compound 1 on Triglycerides in FCS patients

Figure 5    Effect of Compound 1 on Triglycerides in Type V patients

USES OF DGAT1 INHIBITORS

This application is a 371 of PCT/US2011/030234 filed on Mar. 29, 2011, which claims benefit of U.S. Provisional Application No. 661/318814 filed on Mar. 30, 2010, which in its entirety is herein incorporated by reference.

The present invention relates to the use of a DGAT1 inhibitor, or a pharmaceutically acceptable salt or ester thereof, for the treatment of, or the prevention, delay of progression, or treatment of a disease or condition which is selected from chylomicronemia syndrome, familial chylomicronemia syndrome and Type V hyperlipoproteinemia. The present invention further relates to the use of a pharmaceutical composition comprising a DGAT1 inhibitor, or a pharmaceutically acceptable salt or ester thereof, for the prevention, delay of progression, or treatment of a disease or condition which is selected from chylomicronemia syndrome, familial chylomicronemia syndrome and Type V hyperlipoproteinemia.

Hyperlipidemia, or the presence of elevated levels of lipids in the bloodstream, can take the form of hypercholesterolemia (elevated cholesterol), hypertriglyceridemia (elevated triglyceride) or a combination of the two. Hypercholesterolemia, which can further be subdivided, is typically associated with increased risk of atherosclerosis cardiovascular disease. Hypertriglyceridemia occurs when the body's production or intake of triglyceride exceeds the body's ability to metabolize or remove the triglyceride from the bloodstream. The most severe form of hypertriglyceridemia is chylomicronemia (also called hyperchylomicronemia), and is associated with an increased risk of pancreatitis. Chylomicrons are lipoprotein particles that carry absorbed dietary fat from the gut to other body tissues via the bloodstream, and are typically present only during meal times. Chylomicronemia is defined as having the presence of chylomicrons in the bloodstream during times of fasting, and is typically associated with total plasma triglyceride levels above 1000 mg/dL.

The chylomicronemia syndrome refers to a set of clinical complications associated with high chylomicron levels. Typically, patients with the chylomicronemia syndrome have markedly elevated fasting triglyceride levels (1000-2000 mg/dL) with profound excursions (up to 5000 mg/dL and higher) following oral fat intake. The massively elevated plasma triglyceride levels are associated with a number of clinical findings and complications including recurrent episodes of pancreatitis, deposition of triglycerides in the skin in the form of eruptive xanthomas, hepatosplenomegaly, a milky pink appearance of the blood vessels in the back of the eye (lipemia retinalis), and mild neuro-cognitive deficits.

Figure 1:
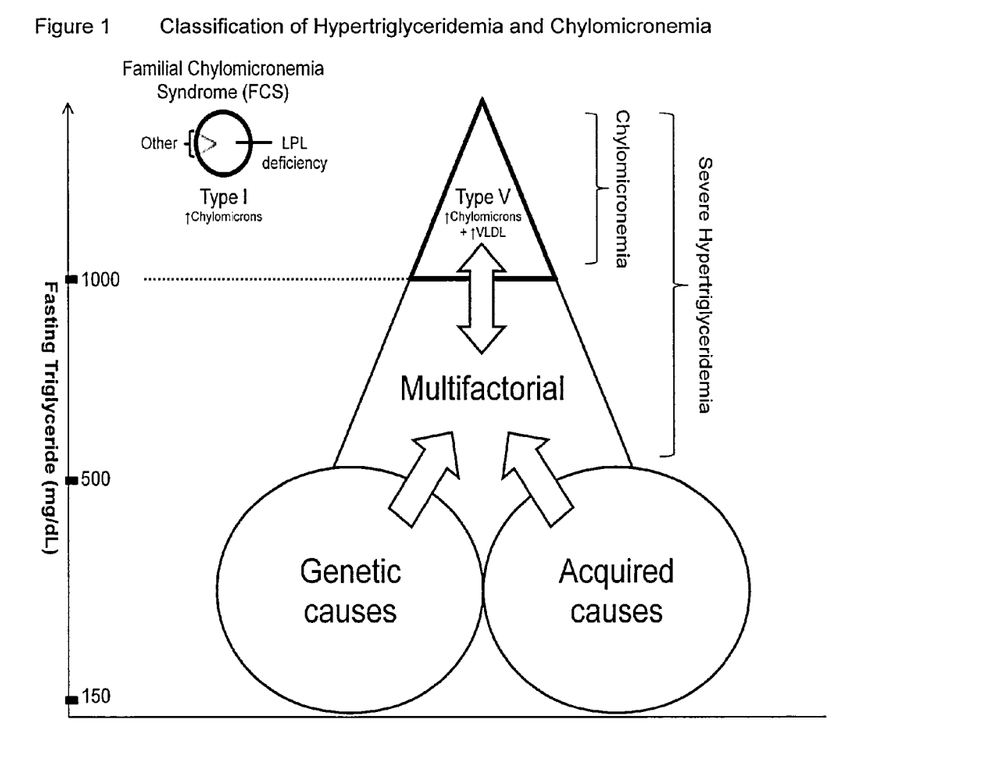

The chylomicronemia syndrome can be further subdivided into two groups (FIG. 1) based on ultracentrifugation of lipoprotein species (see "A system for phenotyping hyperlipoproteinemia", Fredrickson D. S., Lees R. S. *Circulation*, 1965 March; 31, pp. 321-327). Fredrickson classification Type I, also known as the familial chylomicronemia syndrome (FCS), patients have accumulation of only chylomicrons in the bloodstream whereas Fredrickson classification Type V, also known as Type V hyperlipoproteinemia, patients have accumulation of both chylomicrons and very low density lipoproteins (VLDL) in the bloodstream.

The familial chylomicronemia syndrome (FCS or Type I hyperlipoproteinemia) is caused by a homozygous or compound heterozygous defect in the clearance of chylomicrons from the bloodstream. The most common cause of FCS is a defect in lipoprotein lipase (LPL), the protein that hydrolyzes triglycerides carried on chylomicrons. Other causes of FCS include defects in apolipoprotein CII (apoCII, a co-activator of LPL) or glycosylphosphatidylinositol-anchored high-density lipoprotein-binding protein 1 (GPIHBP1, an anchoring protein of LPL).

Type I patients are usually identified by early onset as youth of hypertriglyceridemia and pancreatitis. Thus, patients with FCS typically present in childhood with massively elevated triglyceride levels (>2,000 mg/dL), and recurrent bouts of abdominal pain due to pancreatitis. Into adulthood, the triglyceride levels remain elevated, and patients typically experience multiple episodes of abdominal pain and pancreatitis, which can result in hospitalization and death. Patients also experience other manifestations including eruptive xanthomas, lipemia retinalis, hepatosplenomegaly, and mild neuro-cognitive deficits. The main therapeutic goal in FCS treatment is to prevent or treat pancreatitis via the reduction of triglycerides.

Unfortunately, standard lipid-lowering therapies, such as fibrates, omega-3 fatty acids, statins, and nicotinic acid derivatives (niacin), are not effective in lowering triglycerides in patients with FCS. Therefore, the standard of care therapy for FCS patients is a very low fat diet (≤10% by calories), something which is very difficult to stay compliant with throughout a lifetime [The Familial Chylomicronemia Syndrome. Santamarina-Fojo S. Lipid Disorders 1998. 27(3): 551-567].

Another approach to treat FCS that is under investigation is gene therapy using a replication-deficient Adeno-Associated Viral vector to deliver a naturally-occurring, 'beneficial' variant of LPL (Glybera®) intramuscularly. However this treatment is only transiently effective and requires immunosuppression with mycophenolate, cyclosporine, and steroids [Alipogene tiparvovec, and adeno-associated virus encoding the Ser(447)X variant of human lipoprotein lipase gene for the treatment of patients with lipoprotein lipase deficiency. Burnett J R., Hooper A J. Curr Opin Mol Ther 2009. 6:681-691].

At present there is thus no effective pharmacotherapy for treating FCS and there is thus a need for new methods of treating familial chylomicronemia syndrome (FCS), also known as Type I hyperlipoproteinemia.

Type V hyperlipoproteinemia patients represent a second group at risk for the chylomicronemia syndrome and are usually diagnosed by severe hypertriglyceridemia as adults. This is a heterogenous group at the extreme end of a spectrum of multifactorial hypertriglyceridemia. Patients with Type V hyperlipoproteinemia generally have both an underlying genetic cause and one or more acquired causes of hypertriglyceridemia. The underlying genetic causes include well characterized dyslipidemia such as familial combined hyperlipidemia (Type IIA), dysbetalipoproteinemia (Type III) and familial hypertriglyceridemia (Type VI), and a group of less well characterized dyslipidemias (e.g. heterozygous LPL deficiency, defects in apoA & apoC genes, defects in fatty acid binding and transport proteins). Acquired causes of hypertriglyceridemia include comorbid diseases (e.g. type 2 diabetes, obesity, insulin resistance, lipodystrophy, hypothyroidism), medications (e.g. beta blockers, thiazide diuretics, estrogen, glucocorticoids, transplant medications), and other factors (e.g. pregnancy, alcohol intake).

The primary goal of therapy in Type V patients is to reduce the triglyceride levels, and therefore reduce the risk of pancreatitis. Most patients can be successfully treated by addressing the underlying acquired cause(s) of the elevated triglycerides, such as reducing the amount of dietary fat intake, treating uncontrolled co-morbid diseases such as T2DM (Type 2 diabetes mellitus), discontinuing offending medications, and initiating lipid lowering medications such as fibrates, omega-3 fatty acids, or nicotinic acid derivatives (niacin) [Chylomicronemia Syndrome. Chait A., Brunzell J. Adv Intern Med 1992. 37:249-73.].

Despite optimal therapy, some Type V patients continue to have elevated triglyceride levels. There is thus a need for new methods of treating Type V hyperlipoproteinemia.

SUMMARY OF THE INVENTION

The present inventors have found that a DGAT1 inhibitor, or a pharmaceutically acceptable salt or ester thereof, reduces postprandial triglyceride levels to a clinically significant extent, in patients, specially patients with the chylomicronemia syndrome (including patients with familial chylomicronemia syndrome and patients with Type V hyperlipoproteinemia).

The present invention thus provides a DGAT1 inhibitor, or a pharmaceutically acceptable salt or ester thereof, for use in the prevention, delay of progression, or treatment of a disease or condition which is selected from chylomicronemia syndrome, familial chylomicronemia syndrome, and Type V hyperlipoproteinemia.

There is also provided a DGAT1 inhibitor, or a pharmaceutically acceptable salt or ester thereof, for use in the reduction of postprandial triglyceride levels in patients suffering from a disease or condition which is selected from chylomicronemia syndrome, familial chylomicronemia syndrome, and Type V hyperlipoproteinemia.

There is also provided a DGAT1 inhibitor, or a pharmaceutically acceptable salt or ester thereof, for use in the prevention, delay of progression or treatment of pancreatitis in patients suffering from a disease or condition which is selected from chylomicronemia syndrome, familial chylomicronemia syndrome, and Type V hyperlipoproteinemia.

There is also provided a DGAT1 inhibitor, or a pharmaceutically acceptable salt or ester thereof, for use in the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits. In another embodiment, there is provided a DGAT1 inhibitor is for use in the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits, in patients suffering from a disease or condition which is selected from chylomicronemia syndrome, familial chylomicronemia syndrome, and Type V hyperlipoproteinemia.

In another aspect of the invention, there is provided a pharmaceutical composition, comprising a DGAT1 inhibitor, or a pharmaceutically acceptable salt, or ester thereof, for use in the prevention, delay of progression or treatment of a disease or condition which is selected from chylomicronemia syndrome, familial chylomicronemia syndrome, and Type V hyperlipoproteinemia.

There is also provided a pharmaceutical composition, comprising a DGAT1 inhibitor, or a pharmaceutically acceptable salt, or ester thereof, for use as defined above.

In another aspect, there is also provided a method for the prevention, delay of progression, or treatment of a disease or condition which is selected from chylomicronemia syndrome, familial chylomicronemia syndrome, and Type V hyperlipoproteinemia, comprising administration of a therapeutically effective amount, or a prophylactically effective amount, of a DGAT1 inhibitor, or a pharmaceutically acceptable salt or ester thereof, to a subject, e.g. a human subject, in need of such treatment.

There is also provided a method for the reduction of postprandial triglyceride levels in patients suffering from a disease or condition which is selected from chylomicronemia syndrome, familial chylomicronemia syndrome, and Type V hyperlipoproteinemia, comprising administration of a therapeutically effective amount of a DGAT1 inhibitor, or a pharmaceutically acceptable salt or ester thereof, to a subject, e.g. a human, in need of such treatment.

There is also provided a method for the prevention, delay of progression or treatment of pancreatitis in patients suffering from a disease or condition which is selected from chylomicronemia syndrome, familial chylomicronemia syndrome, and Type V hyperlipoproteinemia, comprising administration of a therapeutically effective amount of a DGAT1 inhibitor, or a pharmaceutically acceptable salt or ester thereof, to a subject, e.g. a human, in need of such treatment.

There is also provided a method for the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits, comprising administration of a therapeutically effective amount of a DGAT1 inhibitor, or a pharmaceutically acceptable salt or ester thereof, to a subject, e.g. a human, in need of such treatment.

In another embodiment, there is provided a method for the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits, comprising administration of a therapeutically effective amount of a DGAT1 inhibitor, or a pharmaceutically acceptable salt or ester thereof, to a human subject suffering from a disease or condition which is selected from chylomicronemia syndrome, familial chylomicronemia syndrome, and Type V hyperlipoproteinemia.

The present invention thus provides the use of a DGAT1 inhibitor, or a pharmaceutically acceptable salt or ester thereof, for the manufacture of a medicament for the prevention, delay of progression, or treatment of a disease or condition which is selected from chylomicronemia syndrome, familial chylomicronemia syndrome, and Type V hyperlipoproteinemia.

The present invention thus provides the use of a DGAT1 inhibitor, or a pharmaceutically acceptable salt or ester thereof, for the manufacture of a medicament for the prevention, delay of progression, or treatment of a disease or condition which is selected from chylomicronemia syndrome, familial chylomicronemia syndrome, and Type V hyperlipoproteinemia.

There is also provided the use of a DGAT1 inhibitor, or a pharmaceutically acceptable salt or ester thereof, for the manufacture of a medicament for one or more of the following purposes:

(a) the reduction of postprandial triglyceride levels in patients suffering from a disease or condition which is selected from chylomicronemia syndrome, familial chylomicronemia syndrome, and Type V hyperlipoproteinemia;

(b) the prevention, delay of progression or treatment of pancreatitis in patients suffering from a disease or condition which is selected from chylomicronemia syndrome, familial chylomicronemia syndrome, and Type V hyperlipoproteinemia;

(c) the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits;

(d) the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits, in patients suffering from a disease or condition which is selected from chylomicronemia syndrome, familial chylomicronemia syndrome, and Type V hyperlipoproteinemia.

In another aspect, there is provided a pharmaceutical composition for the prevention, delay of progression or treatment of a disease or condition which is selected from chylomicronemia syndrome, familial chylomicronemia syndrome, and Type V hyperlipoproteinemia, comprising as active ingredient a DGAT1 inhibitor, or a pharmaceutically acceptable salt or ester thereof.

The present invention also relates to a use of a DGAT1 inhibitor, or a pharmaceutically acceptable salt or ester thereof, to reduce postprandial triglyceride levels in patients, especially patients with the chylomicronemia syndrome, familial chylomicronemia syndrome or Type V hyperlipoproteinemia.

In another aspect of the invention, the present invention relates to a use of a DGAT1 inhibitor, or a pharmaceutically acceptable salt or ester thereof; or a pharmaceutical composition comprising a DGAT1 inhibitor, or a pharmaceutically acceptable salt or ester thereof, for the prevention, delay of progression, or treatment of pancreatitis (e.g. recurrent episodes of pancreatitis), deposition of triglycerides in the skin in the form of eruptive xanthomas, hepatosplenomegaly, the deposition of milky white triglyceride in the blood vessels in the back of the eye (lipemia retinalis), and mild neuro-cognitive deficits, specially in patients suffering from chylomicronemia syndrome, familial chylomicronemia syndrome, and Type V hyperlipoproteinemia.

DETAILED DESCRIPTION OF THE INVENTION

Brief Description of the Figures

The classification of hypertriglyceridemia and chylomicronemia is described in FIG. 1.

The methods and compositions of the present invention comprise a DGAT1 inhibitor, or a pharmaceutically acceptable salt or ester thereof. The DGAT1 inhibitor useful in the compositions of the present invention may be any DGAT1 inhibitor known in the art.

For example, the DGAT1 inhibitor may be chosen from those described in WO2007/126957 and in WO2009/040410.

The DGAT1 inhibitor may be peptidal or non-peptidal in nature, however, the use of a non-peptidal DGAT1 inhibitor is preferred.

Alternatively, the DGAT1 inhibitor may be chosen from the DGAT1 inhibitors described in:
WO2004047755; WO0204682: Polymorphisms In A Diacylglycerol Acyltransferase Gene, And Methods Of Use Thereof; WO9745439: DNA Encoding Acylcoenzyme A: Cholesterol Acyltransferase And Uses Thereof; US20030154504: Methods And Compositions For Modulating Carbohydrate Metabolism; US20030167483: Diacylglycerol O-acyltransferase; WO9967403: Diacylglycerol O-acyltransferase; WO9967268: Diacylglycerol O-acyltransferase; WO05013907: Pyrrolo[1,2-b]pyridazine Derivatives; WO05044250: Use Of Sulfonamide Compounds For The Treatment Of Diabetes And/or Obesity; WO06064189: Oxadiazole Derivatives As DGAT Inhibitors; WO06004200:Urea Derivative; WO06019020: Substituted Ureas; US20040209838: Modulation Of Diacylglycerol Acyltransferase 1 Expression; US20040185559: Modulation Of Diacylglycerol Acyltransferase 1 Expression; WO04047755: Fused Bicyclic Nitrogen-containing Heterocycles; US20040224997: Preparation And Use Of Aryl Alkyl Acid Derivatives For The Treatment Of Obesity; WO05072740: Anorectic Compounds; JP2006045209: Urea Derivative; WO06044775: Preparation And Use Of Biphenyl-4-yl-carbonylamino Acid Derivatives For The Treatment Of Obesity; JP2004067635: DGAT Inhibitor; JP2005206492: Sulfonamide Compound; and U.S. Pat. No. 6,100,077: Isolation Of A Gene Encoding Diacylglycerol Acyltransferase; or a pharmaceutically acceptable thereof.

Alternatively the DTAGT1 inhibitor may be chosen from the DGAT1 inhibitors described in:
WO2004047755;
WO2005013907;
WO2006082952; WO2006004200; WO2006044775; WO2006113919;
WO2006120125; WO2006134317;
WO2007060140; WO2007071966; WO2007137103; WO2007137107;
WO07138304; WO07138311; WO07141502;
WO07141517; WO07141538; WO07141545; WO07144571;
WO2008011130; WO 2008011131; WO08129319; WO08067257;
WO08134690; WO08134693; WO2008141976; WO08148840;
WO2008148849; WO08148851; WO2008148868;
WO2009011285; WO2009016462; WO2009024821; WO2009071483;
WO2009081195; WO2009119534; WO2009126624; WO2009126861;
WO2009147170;
WO2010059602; WO 2010059606; WO2010059611; WO2010084979; WO 2010086820; WO2010146395;
JP 2010132590; JP 2010132590;
US20090076275; US20090093497; US20090105273 US20090170864 and
US2010152445.

Compounds of the present invention may be prepared from commercially available reagents employing general synthetic techniques known to those skilled in the art.

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group.

The term "substituted or unsubstituted alkyl" refers to straight- or branched-chain hydrocarbon groups having 1-20 carbon atoms, preferably 1-10 carbon atoms, containing 0 to 3 substituents. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, alkanoyl, alkoxy, alkoxycarbonyl, alkoxycarbonyloxy, alkanoyloxy, thiol, alkylthio, alkylthiono, alkylsulfonyl, sulfamoyl, sulfonamido, carbamoyl, cyano, carboxy, acyl, aryl, alkenyl, alkynyl, aralkyl, aralkanoyl, aralkylthio, arylsulfonyl, arylthio, aroyl, aroyloxy, aryloxycarbonyl, aralkoxy, guanidino, optionally substituted amino, heterocyclyl.

The term "lower alkyl" refers to those alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 4-6 carbon atoms connected by single bonds, e.g., —(CH$_2$)x-, wherein x is 4-6, which may be interrupted with one or more heteroatoms selected from O, S, S(O), S(O)$_2$ or NR, wherein R may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

The term "carboxamide" refers to —C(O)—NHR$_\square$, wherein R$_\square$ is selected from hydrogen, a C$_1$-C$_8$ alkyl group, a cycloalkyl group, a substituted or unsubstituted aryl group, a substituted or unsubstituted heterocyclyl group, and carboxamide is preferably —C(O)—NH$_2$.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.
The term "alkylthio" refers to alkyl-S—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.

The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to H$_2$NS(O)$_2$—, alkyl-NHS(O)$_2$—, (alkyl)$_2$NS(O)$_2$—, aryl-NHS(O)$_2$, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyridyl N-oxide, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents. Exemplary substituents include, but are not limited to, the following:

(a) optionally substituted alkyl;
(b) hydroxyl (or protected hydroxyl);
(c) halo;
(d) oxo, i.e., =O;
(e) optionally substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl;
(o) alkanoyloxy;
(p) aroyloxy;
(q) arylthio;
(r) aryloxy;
(s) alkylthio;
(t) formyl;
(u) carbamoyl;
(v) aralkyl; or
(w) aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The terms "saturated or unsaturated heterocycloalkyl" or "heterocycloalkyl" refers to nonaromatic heterocyclic or heterocyclyl groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyridyl N-oxide, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O) NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

The term "divalent" refers to a residue linked to at least two residues and optionally having further substituents. As an example, within the context of the present invention the expression "substituted or unsubstituted divalent phenyl residue" is considered to be equivalent to the expression "substituted or unsubstituted phenylene residue".

In one embodiment of the present invention, the DGAT1 inhibitor useful in the compositions of the present invention is a compound having the following structure

A-L1-B-C-D-L2-E or a pharmaceutically acceptable salt or ester thereof, wherein

A is a substituted or unsubstituted alkyl, cycloalkyl, aryl, or heterocyclyl group, L1 is selected from the group consisting of:
   an amine group —NH—
   a substituted amine group of the formula —N(CH$_3$)—, —CH$_2$—NH— or —CH$_2$—CH$_2$—NH—,
   an amide group —C(O)—NH—,
   a sulphonamide group —S(O)$_2$—NH—, or
   a urea group —NHC(O)—NH—, B is a substituted or unsubstituted, monocyclic, 5- or 6-membered divalent heteroaryl group, C-D is selected from the following cyclic structures:
   C-D together is a substituted or unsubstituted divalent biphenyl group,
   C is a substituted or unsubstituted divalent phenyl group and D is a single bond,
   C is a substituted or unsubstituted divalent phenyl group, and D is a substituted or unsubstituted divalent nonaromatic monocyclic ring which is selected from a saturated or unsaturated divalent cycloalkyl group or a saturated or unsaturated divalent heterocycloalkyl group,
   C-D together is a spiro residue, wherein
      the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
      the second cyclic component is a cycloalkyl or cycloalkylidenyl residue which is attached to L2, L2 is selected from the group consisting of:
  a single bond,
  a divalent residue having the following structure:

wherein
  a is 0 or 1,
  b is 0 or 1,
  c is 0 or 1,
  d is 0 or 1,
  e is 0 or 1,
  f is 0 or 1,
    with the provisos that (a+b+c+d+e+f)>0, and c=1 if d=1,
  $R^1$, $R^2$, $R^4$ and $R^5$, which can be the same or different, are a substituted or unsubstituted divalent alkyl, cycloalkyl, alkenyl, alkynyl, alkylene, aryl or heterocyclyl residue,
  $R^3$ is H or hydrocarbyl, or $R^3$ and $R^4$ form together with the nitrogen atom to which they are attached a 5- or 6-membered heterocycloalkyl group,
  with the proviso that $R^1$ and $R^2$ are not both alkyl if c=1 and d=e=f=0 and the carbonyl carbon atom is attached to the moiety E,
  an alkylidenyl group which is linked to the moiety D via a double bond, and
E is selected from the group consisting of:
  a sulphonic acid group and derivatives thereof,
  a carboxyl group and derivatives thereof, wherein the carboxyl carbon atom is attached to L2,
  a phosphonic acid group and derivatives thereof,
  an alpha-keto hydroxyalkyl group,
  a hydroxyalkyl group wherein the carbon atom bonded to the hydroxyl group is further substituted with one or two trifluoro-methyl groups,
  a substituted or unsubstituted five-membered heterocyclyl residue having in the ring at least two heteroatoms and at least one carbon atom, wherein
    the at least one carbon atom of the ring is bonded to two heteroatoms;
    at least one of the heteroatoms to which the carbon atom of the ring is bonded is a member of the ring;
    and at least one of the heteroatoms to which the carbon atom of the ring is bonded or at least one of the heteroatoms of the ring is bearing a hydrogen atom;
  with the provisos that
  L2 is not a single bond or a divalent alkyl group if the moiety D is a single bond,
  L2 is not a single bond if the moiety D is an unsubstituted divalent phenyl group and E is a carboxylic acid or a derivative thereof,
  E is not a carboxamide group if L2 comprises an amide group,
  E is not a —COOH group if D is a single bond and L2 is a —N(CH$_3$)—C(O)— group wherein the carbonyl carbon atom is attached to the moiety E,
  L2 is not a divalent N-methyl piperidinyl group if the moiety E is a pyridinyl-1,2,4-triazolyl group.
In one embodiment of the present invention, the DGAT1 inhibitor useful in the compositions of the present invention is a compound having the following structure

A-L1-B-C-D-L2-E or a pharmaceutically acceptable salt or ester thereof, wherein
A is a substituted or unsubstituted alkyl, cycloalkyl, aryl, or heterocyclyl group, L1 is selected from the group consisting of:
  an amine group —NH—
  a substituted amine group of the formula —N(CH$_3$)—, —CH$_2$—NH— or —CH$_2$—CH$_2$—NH—,
  an amide group —C(O)—NH—,
  a sulphonamide group —S(O)$_2$—NH—, or
  a urea group —NHC(O)—NH—,
B is a substituted or unsubstituted, monocyclic, 5- or 6-membered divalent heteroaryl group,
C-D is selected from the following cyclic structures:
  C-D together is a substituted or unsubstituted divalent biphenyl group,
  C is a substituted or unsubstituted divalent phenyl group and D is a single bond,
  C is a substituted or unsubstituted divalent phenyl group, and D is a substituted or unsubstituted divalent non-aromatic monocyclic ring which is selected from a saturated or unsaturated divalent cycloalkyl group or a saturated or unsaturated divalent heterocycloalkyl group,
  C-D together is a Spiro residue, wherein
    the first cyclic component is a benzo-fused cyclic component wherein the ring which is fused to the phenyl part is a 5- or 6-membered ring, optionally comprising one or more heteroatoms, the first cyclic component being attached to the moiety B via its phenyl part, and
    the second cyclic component is a cycloalkyl or cycloalkylidenyl residue which is attached to L2,
L2 is selected from the group consisting of:
  a single bond,
  a divalent residue having the following structure:

wherein
  a is 0 or 1,
  b is 0 or 1,
  c is 0 or 1,
  d is 0 or 1,
  e is 0 or 1,
  f is 0 or 1,
    with the provisos that (a+b+c+d+e+f)>0, and c=1 if d=1,
  $R^1$, $R^2$, $R^4$ and $R^5$, which can be the same or different, are a substituted or unsubstituted divalent alkyl, cycloalkyl, alkenyl, alkynyl, alkylene, aryl or heterocyclyl residue,
  $R^3$ is H or hydrocarbyl, or $R^3$ and $R^4$ form together with the nitrogen atom to which they are attached a 5- or 6-membered heterocycloalkyl group,
  with the proviso that $R^1$ and $R^2$ are not both alkyl if c=1 and d=e=f=0 and the carbonyl carbon atom is attached to the moiety E,
  an alkylidenyl group which is linked to the moiety D via a double bond, and
E is selected from the group consisting of:
  a sulphonic acid group and derivatives thereof,
  a carboxyl group and derivatives thereof, wherein the carboxyl carbon atom is attached to L2,
  a phosphonic acid group and derivatives thereof,
  an alpha-keto hydroxyalkyl group,
  a hydroxyalkyl group wherein the carbon atom bonded to the hydroxyl group is further substituted with one or two trifluoro-methyl groups,
  a substituted or unsubstituted five-membered heterocyclyl residue having in the ring at least two heteroatoms and at least one carbon atom, wherein the at least one carbon atom of the ring is bonded to two heteroatoms;

at least one of the heteroatoms to which the carbon atom of the ring is bonded is a member of the ring;

and at least one of the heteroatoms to which the carbon atom of the ring is bonded or at least one of the heteroatoms of the ring is bearing a hydrogen atom;

with the provisos that

L2 is not a single bond or a divalent alkyl group if the moiety D is a single bond, L2 is not a single bond if the moiety D is an unsubstituted divalent phenyl group and E is a carboxylic acid or a derivative thereof, E is not a carboxamide group if L2 comprises an amide group, E is not a —COOH group if D is a single bond and L2 is a —N(CH₃)—C(O)— group wherein the carbonyl carbon atom is attached to the moiety E, L2 is not a divalent N-methyl piperidinyl group if the moiety E is a pyridinyl-1,2,4-triazolyl group, L2 is not —C(O)—[R⁴]ₑ—[R⁵]f— when C is a substituted or unsubstituted divalent phenyl group and D is a single bond.

In one embodiment of the present invention, the DGAT1 inhibitor useful in the compositions of the present invention is a compound having the following structure

A-Q-B-C-D wherein

A is a substituted or unsubstituted alkyl, substituted or unsubstituted alkoxy, substituted or unsubstituted cycloalkyl, optionally substituted amino, substituted or unsubstituted aryl, substituted or unsubstituted heteroaryl or a substituted or unsubstituted heterocyclyl;

Q is a divalent or trivalent five membered heterocycle or heteroaryl;

B is a substituted or unsubstituted divalent heteroaryl group selected from one of the groups below:

wherein

X₁ and X₂' are independently selected from O, NH, NR₉ or S, wherein R₉ is selected from lower alkyl, lower alkylamino, lower alkoxyalkyl, lower hydroxyalkyl, X₁', X₂, X₃ and X₄ are independently selected from N, or CH, C is wherein R₁ is selected from hydrogen, cyano, lower alkylsulfonylamino, alkanoylamino, halogen, lower alkyl, trifluoromethyl, lower alkoxy, lower alkylamino, lower dialkylamino, and NO₂, R'₁, R₂ and R'₂ are independently selected from hydrogen, halogen, trifluoromethyl, aryloxy, lower alkyl, lower alkoxy, lower alkylamino, lower dialkylamino, and NO₂, or C may also be a substituted or unsubstituted bicyclic aryl or heteroaryl group, D is selected from hydrogen, halogen, hydroxyl, cyano, alkanoylamino, carboxy, carbamoyl, —O-L₂-E, —S-L₂-E', —C(O)—O-L₂-E, -L₂-E", and —NR₆-L₂-E', L₂ is —(CH₂)ₙ—(CR₅R₅')ₚ—(CH₂)ₘ—

E is alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO₂—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido,

E' is alkyl, acyl, alkoxycarbonyl, cycloalkoxycarbonyl, aryloxycarbonyl, heterocyclyloxycarbony, carboxy, carbamoyl, sulfonylcarbamoyl, sulfonyl, —SO₂—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —SO₂—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, R₅ and R₅' are, independently from each other, hydrogen, halogen, hydroxyl, lower alkoxy, or lower alkyl, or R₅ and R₅' are joined together to form a spiro residue of the formula wherein
X' is NR$_x$, O, S or CR$_x$R$_{x''}$ r' and s' are, independently from each other, zero or an integer from 1 to 3, R$_x$ is hydrogen or lower alkyl, R$_{x'}$ is hydrogen, halogen, hydroxyl, alkoxy, or lower alkyl, R$_{x''}$ is hydrogen or lower alkyl; or a stereoisomer, enantiomer or tautomer thereof, a pharmaceutically acceptable salt thereof, or a prodrug thereof.

Unless otherwise indicated, the compounds provided in the formula above are meant to include a pharmaceutically acceptable salt, prodrug, ester, stereoisomer, crystalline form, or polymorph thereof.

In a further embodiment, the above listed compounds are in the form of their corresponding potassium, sodium, hydrochloric, methanesulfonic, phosphoric or sulfuric acids salts. The DGAT1 inhibitors according to the present invention and their salts can be prepared for example by the methods described in WO2007126957 and in WO2009/040410.

In another embodiment, the DGAT1 inhibitor is a compound which is selected from:

(4-{6-[5-(4-Chloro-phenyl)-[1,3,4]oxadiazol-2-yl]-1H-benzoimidazol-2-yl}-3,5-dimethyl-phenoxy)-acetic acid, (3,5-Dichloro-4-{6-[5-(4-chloro-phenyl)-[1,3,4]oxadiazol-2-yl]-1H-benzoimidazol-2-yl}-phenoxy)-acetic acid, 3-(4-{6-[5-(4-Methoxy-phenyl)-[1,3,4]oxadiazol-2-yl]-1H-benzoimidazol-2-yl}-3,5-dimethyl-phenyl)-propionic acid, 3-(4-{6-[5-(3-Chlorophenylamino)-[1,3,4]oxadiazol-2-yl]-1H-benzoimidazol-2-yl}-3,5-dimethylphenyl)-propionic acid, 3-(4-{6-[5-(4-methoxyphenylamino)-[1,3,4]oxadiazol-2-yl]-1H-benzimidazol-2-yl}-3,5-dimethylphenyl)-propionic acid, 3-(4-{6-[5-(4-Chloro-phenyl)-[1,3,4]oxadiazol-2-yl]-1H-benzoimidazol-2-yl}-3,5-dimethyl-phenyl)-propionic acid, 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid,

[3-(4-{6-[5-(4-Chloro-phenyl)-[1,3,4]oxadiazol-2-yl]-1H-benzoimidazol-2-yl}-3,5-dimethyl-phenyl)-propyl]-phosphonic acid, (3-{3,5-Dimethyl-4-[6-(5-phenyl-[1,3,4]oxadiazol-2-yl)-1H-benzoimidazol-2-yl]-phenyl}-propyl)-phosphonic acid,

[3-(4-{6-[5-(4-Methoxy-phenyl)-[1,3,4]oxadiazol-2-yl]-1H-benzoimidazol-2-yl}-3,5-dimethyl-phenyl)-propyl]-phosphonic acid, 3-{4-[6-(5-methoxy-[1,3,4]oxadiazol-2-yl)-1H-indol-2-yl]-3,5-dimethylphenyl}-propionic acid and 3-(3,5-Dichloro-4-{6-[5-(4-chloro-phenyl)-[1,3,4]oxadiazol-2-yl]-1H-benzoimidazol-2-yl}-phenyl)-propionic acid, or a pharmaceutically acceptable salt thereof.

In another embodiment, the DGAT1 inhibitor is a compound which is selected from (4-{6-[5-(4-Chloro-phenyl)-[1,3,4]oxadiazol-2-yl]-1H-benzoimidazol-2-yl}-3,5-dimethyl-phenoxy)-acetic acid, 3-(4-{6-[5-(4-Methoxy-phenyl)-[1,3,4]oxadiazol-2-yl]-1H-benzoimidazol-2-yl}-3,5-dimethyl-phenyl)-propionic acid, 3-(4-{6-[5-(4-methoxyphenylamino)-[1,3,4]oxadiazol-2-yl]-1H-benzimidazol-2-yl}-3,5-dimethylphenyl)-propionic acid, 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid and,

[3-(4-{6-[5-(4-Chloro-phenyl)-[1,3,4]oxadiazol-2-yl]-1H-benzoimidazol-2-yl}-3,5-dimethyl-phenyl)-propyl]-phosphonic acid;

or a pharmaceutically acceptable salt thereof.

In one embodiment, the DGAT1 inhibitor is trans-(4-{-4,5-(6-trifluoromethyl-pyridin-3-ylamino)-pyridin-2-yl]-phenyl}-cyclohexyl)-acetic acid, or a pharmaceutically acceptable salt thereof. In another embodiment, the DGAT1 inhibitor is trans-(4-{4-[5-(6-Trifluoromethyl-pyridin-3-ylamino)-pyridin-2-yl]-phenyl}-cyclohexyl)-acetic acid, sodium salt.

Use of a Pharmaceutical Composition Comprising a DGAT1 Inhibitor

The present invention also provides the use of a pharmaceutical composition comprising a compound as defined above and one or more pharmaceutically acceptable carrier or excipient.

Such a pharmaceutical composition comprises a therapeutically effective amount of DGAT1 inhibitor. Each dosage unit can contain the daily dose or may contain a fraction of the daily dose, such as one-third of the doses.

Particularly, the above composition refers to a composition comprising 0.1 to 1000 mg DGAT1 inhibitor, preferably 0.1 to 300 mg DGAT1 inhibitor, more preferably 1 to 100 mg DGAT1 inhibitor.

In one embodiment, the DGAT1 inhibitor is used at a dose of 5-40 mg, of 10-40 mg, or of 20-40 mg. In another embodiment, the DGAT1 inhibitor is used at a dose of 5, 10, 15, 20, 25, 30 or 40 mg. In a preferred embodiment, the DGAT1 inhibitor is used at a dose of 5, 10, or 20 mg.

It is to be understood that the doses quoted herein refer to the DGAT1-inhibitor itself. When a pharmaceutically acceptable salt of the DGAT1-inhibitor is used, the doses used will need to be adjusted accordingly.

The composition may comprise a pharmaceutically acceptable excipient, e.g. a diluent or carrier. The pharmaceutically acceptable excipient may be selected from the group consisting of fillers, e.g. sugars and/or sugar alcohols, e.g. lactose, sorbitol, mannitol, maltodextrin, etc.; surfactants, e.g. sodium lauryle sulfate, Brij 96 or Tween 80; disintegrants, e.g. sodium starch glycolate, maize starch or derivatives thereof; binder, e.g. povidone, crosspovidone, polyvinylalcohols, hydroxypropylmethylcellulose; lubricants, e.g. stearic acid or its salts; flowability enhancers, e.g. silicium dioxide; sweeteners, e.g. aspartame; and/or colorants, e.g. b-carotene.

A composition for use in the invention may comprise a) 0.1 to 1000 mg DGAT1 inhibitor and optionally pharmaceutically acceptable excipients selected from the group of about 0.1 to about 10 g fillers, about 0.05 to about 3.0 g surfactant, about 0.05 to about 2.0 preferred g disintegrant, about 0.02 to about 2.0 g binder, about 0.001 to about 1.0 g lubricant, about 0.1 to about 5.0 g flowability enhancer, about 0.01 to about 4.0 g sweetener, and about 0.001 to about 0.5 g colorant. The DGAT1 inhibitor is any of the preferred compounds listed above.

In another embodiment, the composition may comprise a) 0.1 to 1000 mg DGAT1 inhibitor and optionally pharmaceutically acceptable excipients selected from the group of about 0.05 to about 10 g fillers, about 0.05 to about 3.0 g surfactant, about 0.05 to about 2.0 g disintegrant, about 0.005 to about 2.0 g binder, about 0.001 to about 1.0 g lubricant, about 0.005 to about 5.0 g flowability enhancer, about 0.01 to about 4.0 g sweetener, and about 0.001 to about 0.5 g colorant. The DGAT1 inhibitor is any of the preferred compounds listed above.

Oral dosage forms are the preferred compositions for use in the present invention and these are the known pharmaceutical forms for such administration, for example tablets, capsules, bars, sachets, granules, syrups and aqueous or oily suspensions. The pharmaceutically acceptable excipients (diluents and carriers) are known in the pharmacist's art. Tablets may be formed from a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound. For example, the tablets and capsules may conveniently each contain the amount of DGAT1 inhibitor as described above.

Other dosage forms for oral administration include, for example, aqueous suspensions containing the active compounds in an aqueous medium in the presence of a non-toxic suspending agent such as sodium carboxymethylcellulose, and oily suspensions containing the active compounds in a suitable vegetable oil, for example arachis oil. The active compounds may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium.

In the compositions of the present invention the active compounds may, if desired, be associated with other compatible pharmacologically active ingredients. Optionally vitamin supplements may be administered with the compounds of the present invention.

The compounds or compositions are administered during a meal or 1-2 hours before or after a meal. In one embodiment, the compounds of the invention are administered 1-2 hours before a meal, preferably before breakfast. In another embodiment, the compounds of the invention are administered once daily, preferably 1-2 hours before a meal.

The above compounds are only illustrative of DGAT1 inhibitors that can be used in the compositions of the present invention. As this listing of compounds is not meant to be comprehensive, the methods of the present invention may employ any DGAT1 inhibitor, and are not limited to any particular structural class of compounds.

The compositions of the present invention may be used in combination with other drugs that may also be useful in the treatment, prevention, or control of obesity, diabetes, diabetes associated with obesity, and diabetes-related disorders for which compounds comprising the compositions are useful.

Such other drugs may be administered, by a route and in an amount commonly used therefore, contemporaneously or sequentially with a composition of the present invention. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that contain one or more other active ingredients, in addition to a compound of the present invention.

In particular, the combination partners may be selected from the ones described in WO2007/126957 and in WO2009/040410. Thus, the other active ingredient may be selected from a pharmaceutical composition comprising a compound selected from an anti-diabetic, a hypolipidemic agent, an anti-obesity agent and an anti-hypertensive agent, or agonists of peroxisome proliferator-activator receptors.

The terms "administration of" and or "administering a" compound should be understood to mean providing a compound of the invention or a prodrug of a compound of the invention to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "therapeutically effective amount" as used herein means the amount of the active compounds in the composition that will elicit the biological or medical response in a tissue, system, subject, or human that is being sought by the researcher, veterinarian, medical doctor or other clinician, which includes alleviation of the symptoms of the disorder being treated.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of chylomicronemia syndrome or familial chylomicronemia syndrome in a subject at risk of developing the disorder.

The magnitude of prophylactic or therapeutic dose of the active ingredients of the composition will, of course, vary with the nature of the severity of the condition to be treated and with the particular compound in the composition and its route of administration. It will also vary according to the age, weight and response of the individual patient.

In general, the daily dose range of the DGAT1 inhibitor lies within the range of from about 0.0001 mg/kg to about 100 mg/kg, preferably from about 0.001 mg/kg to about 50 mg/kg body weight of a subject in single or divided doses. In one embodiment, the daily dose range of the DGAT1 inhibitor is from about 0.01 mg/kg to about 40 mg/kg, preferably from about 0.01 mg/kg to about 20 mg/kg body weight of a subject in single or divided doses. On the other hand, it may be necessary to use dosages outside these limits in some cases.

In the case where an oral composition is employed, a suitable dosage range is, e.g. from about 0.001 mg/kg to about 100 mg/kg of each compound in the composition per day, preferably from about 0.01 mg to about 2000 mg per day. For oral administration, the compositions are preferably provided in the form of tablets containing from 0.01 mg to 2,000 mg, e.g. 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850, 1,000 and 2,000 milligrams of each active ingredient for the symptomatic adjustment of the dosage to the subject to be treated. This dosage regimen may be adjusted to provide the optimal therapeutic response. For example, the DGAT1-inhibitor may be administered once daily over a period of several days or several (1, 2, 3, 4, or more) weeks. In another embodiment, the DGAT1-inhibitor is administered once, or several (e.g. 1, 2, 3) times daily.

Method of Assessing the Activity of a DGAT1 Inhibitor

The activity of compounds as DGAT1 inhibitors according to the invention may for example be assessed by the following methods or methods described in WO2007/126957.

EXAMPLE 1

Effect of Compound 1 on Plasma Triglycerides in a Model of Severe Hypertriglyceridemia

Example 1 demonstrates that DGAT1 inhibitors have been shown to reduce postprandial triglyceride levels in severely hypertriglyceridemic animals (STZ rats).

Compound 1 was shown to be effective in blunting an increase in plasma triglycerides in a model of severe hypertriglyceridemia as described below.

Materials and Methods

Male Sprague Dawley (SD) rats at 12 wks of age were studied. Orlistat (04139-100MG) and Streptozotocin (S0130-1G) were purchased from Sigma (St. Louis, Mo.).

The chemical structure of compound 1, trans-4-[4-[5-[[6-(trifluoromethyl)-3-pyridinyl]amino]-2-pyridinyl]phenyl] cyclohexane acetic acid, sodium salt is shown below:

Compound 1 was synthesized according to the methods described in WO2007126957.

Compound Preparation

Compounds were suspended in vehicle (0.5% methyl cellulose with 0.1% Tween-80) to achieve a dosing volume of 4 ml/kg and dosing concentration of 10 mpk for both compound 1 and orlistat (Sigma, St. Louis, Mo.).

Pre-Study Animal Preparation

Two weeks into consuming a 60% high fat diet, animals were treated with a 40 mpk dose of streptozotocin (STZ given intravenously (iv) in 10 mM sodium citrate in normal saline, pH=4.5). Nine days later, animals were assigned to three experimental groups (vehicle, compound 1 at 10 mpk, or orlistat at 10 mpk) on the basis of 6 hr fasted TG concentrations (n=10/group). On the morning of the study, 14 days after animals were placed in experimental groups, animals were fasted for 6 hours, after which studies commenced at 1100 hr with baseline blood collected by tail nick into ethylenediaminetetraacetic acid-lined tubes (Sarstedt, Nümbrecht, Germany).

Administration of Drugs and Blood Collection

The baseline blood sample (80 μl) was collected immediately prior to administering compounds. Rats were orally gavaged with drug or vehicle (4 ml/kg) beginning at 1100 hrs. Thirty minutes later, Intralipid was orally gavaged at 10 ml/kg to all rats, representing t=0 hr. At 2 and 4 hrs post-Intralipid, tail nick blood samples were taken to assess plasma TGs.

Blood Sample Handling and Analyses

Blood samples remained on ice following collection for no longer than 30 min prior to centrifugation (10 min, 4° C., 1000 g) and resulting plasma was aliquoted for plasma TG analysis.

Calculations

Plasma TGs (triglycerides) (corrected for glycerol) were compared on an absolute basis, as a percent change from baseline (% TGs), and as area above baseline over 0-4 hours (AABtg0-4-h) using the Trapezoidal rule. Percent change from baseline was calculated as follows:

% change from baseline=($[TGs]$ at 2 or 4 hrs)−($[TGs]$ at baseline)*100 $[TGs]$ at baseline Statistical Analyses Data are reported as means±SEM. One-way ANOVA (analysis of variance) assessed between-group differences when any comparisons that were not time-dependent were made (body weight, pre-study plasma TGs, AABtg0-4-h). To assess that the Intralipid bolus produced a significant increase in plasma TGs in the vehicle group, a repeated measures (RM) one-way ANOVA was used with Tukey's posthoc test applied to compare plasma parameter means at 2 and 4 hrs vs. pre-treatment concentrations. RM two-way ANOVA was used to assess the significance of the treatment-by-time interaction for plasma parameters (TGs and % TGs) followed by Bonferroni's t-test to compare differences among the groups. Outliers were determined using the Grubb's Test for Outliers. Significance was set at P≤0.05.

Results

Figure 2:
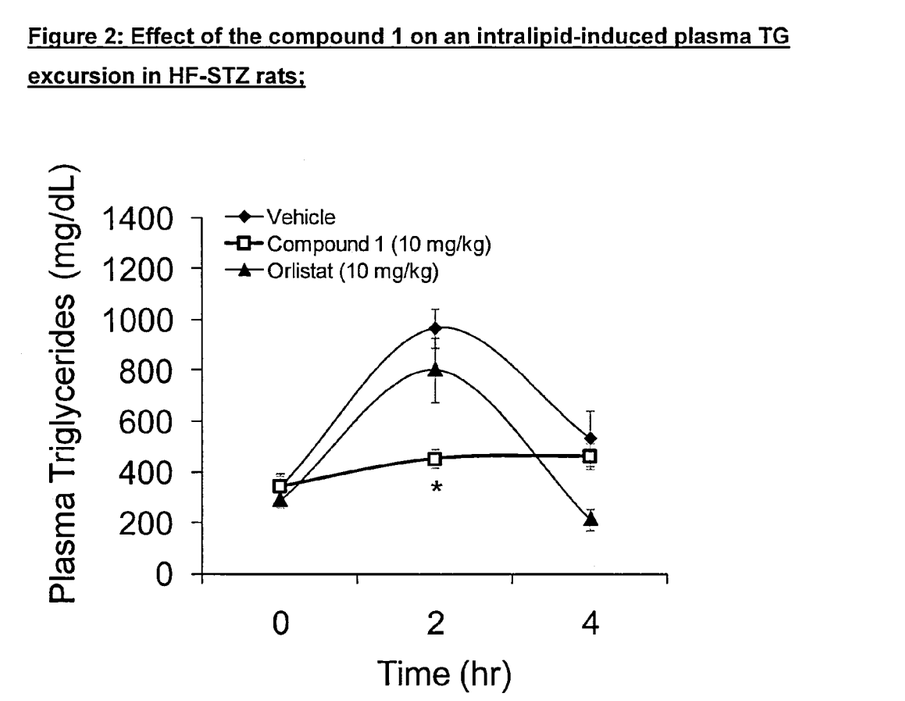
FIG. 2 shows the effect of a DGAT1 inhibitor on plasma triglycerides in a model of severe hypertriglyceridemia.

Oral gavage of Intralipid at 10 ml/kg produced a significant plasma TG excursion (FIG. 2) such that in the vehicle group, plasma TG concentrations at 2 and 4 hrs were higher than pre-dosing values (P≤0.001). At 2 hrs, plasma TGs were significantly lower in the compound 1 group compared to vehicle and orlistat groups (P≤0.001, indicated by asterisk in FIG. 2). By 4 hrs, plasma TGs did not differ between the compound 1 and vehicle treated groups, while plasma TGs in the orlistat-treated animals were lower than the other 2 groups (P≤0.001).

| Treatment | Pre-dose TG (mg/dL) | Plasma TG (mg/dL) at 2 hrs | Plasma TG (mg/dL) at 4 hrs |
| --- | --- | --- | --- |
| Vehicle | 339.2 ± 42.8 | 966.2 ± 74.9 | 531.3 ± 108.6 |
| Compound 1 | 346.1 ± 49.6 | 494.5 ± 54.2 | 461.5 ± 52.5 |
| Orlistat | 288.4 ± 27.4 | 891.8 ± 97.8 | 236.3 ± 37.9 |

EXAMPLE 2

Blunting an Increase in Plasma Triglycerides in a Model of Impaired Triglyceride Clearance Example 2 demonstrates that DGAT1 inhibitors reduce the formation rate of chylomicrons in animals where LPL has been inactivated (Triton rat).

Materials and Methods

Male Sprague Dawley rats were studied at 9 and 10 weeks of age and were overnight fasted the night prior to study. The compound treated groups received a suspension of compound 1 at 10 mg/kg administered in 0.5% methyl cellulose with 0.1% Tween-80 at 4 mg/kg. Vehicle treated groups were dosed in a volume-matched manner with 0.5% methyl cellulose with 0.1% Tween-80. Vehicle and compounds were made up in a single batch the day before the start of each study. Orlistat was administered as a suspension in 0.5% methyl cellulose with 0.1% Tween-80 at 4 mL/kg. Intralipid was used as a high fat meal. Triton WR-1339 (10% weight: weight) was dissolved in normal saline and dosed at 100 mg/kg (i.v.) at a volume of 1 mL/kg.

A baseline blood sample was collected by tail nick into ethylenediaminetetraacetic acid-lined tubes (Sarstedt, Nümbrecht, Germany) immediately prior to administering compounds (between 0830 and 0900 hrs). Rats were gavaged with drug or vehicle (4 mL/kg) beginning at 0830 hrs. Thirty minutes later, Intralipid was gavaged at 10 mL/kg to all rats, representing t=−30 min. Again, thirty minutes later, representing time=0 min, all rats were dosed via tail vein with Triton WR-1339 (100 mg/kg and 1 mL/kg) in normal saline. Blood samples were taken at −30 minutes (immediately prior to Intralipid/water dosing), −15 minutes, 0 minutes (immediately prior to Triton WR-1339 administration), as well as at 30, 60, 90, 120, and 240 minutes following administration of Triton WR-1339. Blood samples remained on ice following collection for no longer than 30 min prior to centrifugation. Following centrifugation (10 min, 4° C., 1000×g), plasma was aliquoted for plasma TG analysis.

Statistical Analyses

Data are reported as means±SEM. Repeated measures two-way ANOVA was used to assess the significance of the treatment by time interaction in plasma TGs followed by Tukey's post-hoc test to compare differences among the groups. Significance was set at $P<0.05$ and represented as asterisks in FIG. 3.

Results

Figure 3:
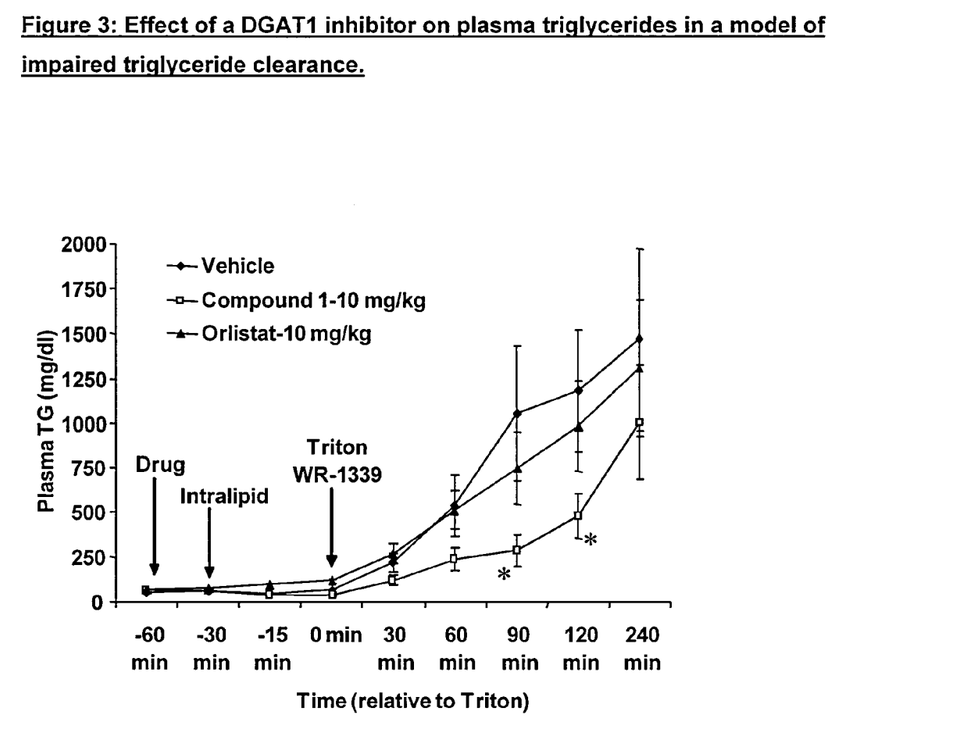
FIG. 3 shows the effect of a DGAT1 inhibitor on plasma triglycerides in a model of impaired triglyceride clearance.

Compound 1 treatment resulted in significantly decreased plasma TG appearance compared to vehicle and orlistat treatments following an Intralipid bolus at 90 and 120 minutes post Triton WR-1339 administration ($P \leq 0.05$, FIG. 3).

| Treatment | Pre-Triton TG (mg/dL) | Plasma TG (mg/dL) at 90 min | Plasma TG (mg/dL) at 120 min |
|---|---|---|---|
| Vehicle | 66.0 ± 9.4 | 1053 ± 377.8 | 1180 ± 339.0 |
| Compound 1 | 35.6 ± 5.6 | 290.2 ± 89.7 | 479.3 ± 123.4 |
| Orlistat | 114.5 ± 13.0 | 747.3 ± 203.7 | 984.9 ± 251.7 |

These data indicate that compound 1 suppresses the rate of absorption of triglycerides arising from a high fat meal.

EXAMPLE 3

Tablet Comprising a DGAT1 Inhibitor

The following are examples of a representative pharmaceutical dosage form suitable for use in the present invention: Uncoated Tablet Comprising a DGAT1 Inhibitor, (5 Mg of Active Ingredient, Based on Free Acid of Compound 1)

| Ingredients | mg/tab |
|---|---|
| trans-(4-{4-[5-(6-Trifluoromethyl-pyridin-3-ylamino)-pyridin-2-yl]-phenyl}-cyclohexyl)-acetic acid, sodium salt | 5.26 |
| Microcrystalline Cellulose | 86.24 |
| Crospovidone | 7.0 |
| Colloidal silicon dioxide | 0.5 |
| Magnesium Stearate | 1.0 |
| Total weight | 100 mg |

Uncoated Tablet Comprising a DGAT1 Inhibitor (Based on 10 Mg of Active Ingredient, Based on Free Acid of Compound 1)

| Ingredients | mg/tab |
|---|---|
| trans-(4-{4-[5-(6-Trifluoromethyl-pyridin-3-ylamino)-pyridin-2-yl]-phenyl}-cyclohexyl)-acetic acid, sodium salt | 10.51 |
| Microcrystalline Cellulose | 172.49 |
| Crospovidone | 14.0 |
| Colloidal silicon dioxide | 1.0 |
| Magnesium Stearate | 2.0 |
| Total weight | 200 mg |

Preparation Process trans-(4-{4-[5-(6-Trifluoromethyl-pyridin-3-ylamino)-pyridin-2-yl]-phenyl}-cyclohexyl)-acetic acid, sodium salt along with Microcrystalline Cellulose (partial), and Crospovidone (intragranular) are mixed in a low shear mixer. The mixed contents, along with remaining Microcrystalline Cellulose are passed through an oscillating mill equipped with a suitable screen. The screened contents are mixed in a low shear mixer for a suitable amount of time. Colloidal silicon dioxide, screened through an appropriate screen is mixed with the blend from earlier step and the contents are mixed for a suitable amount of time. Magnesium Stearate, screened through a suitable screen size is added to the preblend and mixed for a suitable amount of time. The lubricated intragranular preblend is passed through a roller compaction system for densification at the optimized parameters for feed rate, roll speed and roll force. The ribbons from the process are collected and passed through an oscillating mill equipped with a suitable screen to get the desired milled material. The milled material is then mixed with extragranular prescreened Crospovidone and mixed in a low shear mixer for a suitable amount of time. To the mixture, prescreened Magnesium Stearate is added and mixed for a suitable amount of time. The final blend is then compressed to the desired tablet weight to achieve the optimized thickness, hardness and disintegration time.

EXAMPLE 4

An open-label, multiple-dose, parallel group clinical study is carried out to assess the safety, tolerability, pharmacokinetics and pharmacodynamics of compound 1 in twelve patients with chylomicronemia (six with FCS and six with Type V).

Materials and Methods

The safety and tolerability of multiple doses of Compound 1 in patients with chylomicronemia (both FCS and Type V), and the effect of oral Compound 1 on fasting and postprandial plasma triglycerides in the study population are determined using the following method.

The clinical study is an open-label, out-patient parallel group study to assess the safety, tolerability, pharmacokinetics and pharmacodynamics of Compound 1 administered once daily for 21 days in patients with chylomicronemia (both FCS and Type V). Six patients of each phenotype are enrolled and treated with Compound 1 at 20 mg per day for 21 days. Following a screening period of up to 90 days, eligible patients undergo a 7-day baseline period, a 21-day treatment period, a 14-day follow-up period after last treatment day and a study completion evaluation.

The enrolling criteria for Type V patients is a screening baseline of greater than or equal to 1000 mg/dL fasting triglycerides (TG), and a documented history of heterozygous lipoprotein lipase deficiency. The enrolling criteria for familial chylomicronemia syndrome (FCS) patients is a screening baseline of greater than or equal to 1000 mg/dL fasting triglycerides, and a documented history of homozygous lipoprotein lipase deficiency.

Patients are seen at a screening visit, and, if found to meet enrollment criteria, are enrolled in the study. At this time they are given instructions to adhere to a very low fat diet (<15 g/day) during the duration of the study, as is the standard of care for this population. Patients are also provided with three days' worth of standardized very low fat meals that are consumed for the three days prior to baseline evaluation (Day—4, Day—3, & Day—2)

Patients arrive at the study site on Day—1 early morning after an overnight fast for a meal tolerance test (MTT) to evaluate baseline postprandial triglyceride (TG) response. The MTT is a liquid meal of approximately 700 kcal, being 13% fat, 65% carbohydrates and 22% protein. Before the MTT, and at hourly time points through 9 hours, blood samples are taken for triglyceride and other metabolic measurements. Patients are discharged after completing this assessment and return to the study site next morning (Day 1) for a blood collection approximately 24 hours post meal, before the first dose of the study drug (Compound 1 tablets) is administered.

On the morning of Day 1, patients receive the first dose of Compound 1 at the clinic site. The drug supply for remainder of the 21-day treatment period is provided to the patients, who are instructed to take the drug orally once daily approximately one hour before breakfast for 21 days. Patients are also instructed to continue adherence to a very low fat diet. Patients are then released to home.

Patients report to the study site once weekly during the treatment period for safety and pharmacokinetics assessment, drug accountability and reviewing the meal plan and food diary. Additionally, the site staff contacts patients by phone, at least once between the clinic visits to check patients' wellbeing and monitor compliance with drug administration and low-fat meals instructions.

Patients are given pre-prepared very low-fat meals again that are consumed on Day 18, 19 & 20. Patients return to the study site on Day 21 early morning after an overnight fast for a second test meal (MTT) and frequent blood samples collection to evaluate postprandial TG response. Following the MTT and associated Day 21 assessments, patients are discharged to home. They return on the morning of Day 22 for a 24 h blood sample for triglycerides.

Results

Compound 1 treatment was safe and well tolerated by all 12 patients who received treatment at 20 mg daily for 3 weeks.

After 3 weeks of treatment with Compound 1, triglyceride levels were decreased in both groups of patients.

TABLE 1

Effect of Compound 1 on Triglycerides in FCS patients

| Parameter for Type I patients (n = 6) | Mean Baseline | Mean Δ from Baseline |
|---|---|---|
| Fasting TG | 1968.0 mg/dL | −38.4% |
| Postprandial Peak TG | 1913.1 mg/dL | −36.4% |
| Postprandial TG $AUC_{0-9}$ | 15044.5 mg * h/dL | −35.4% | mg * h/dL = mg hour/dL

Figure 4:
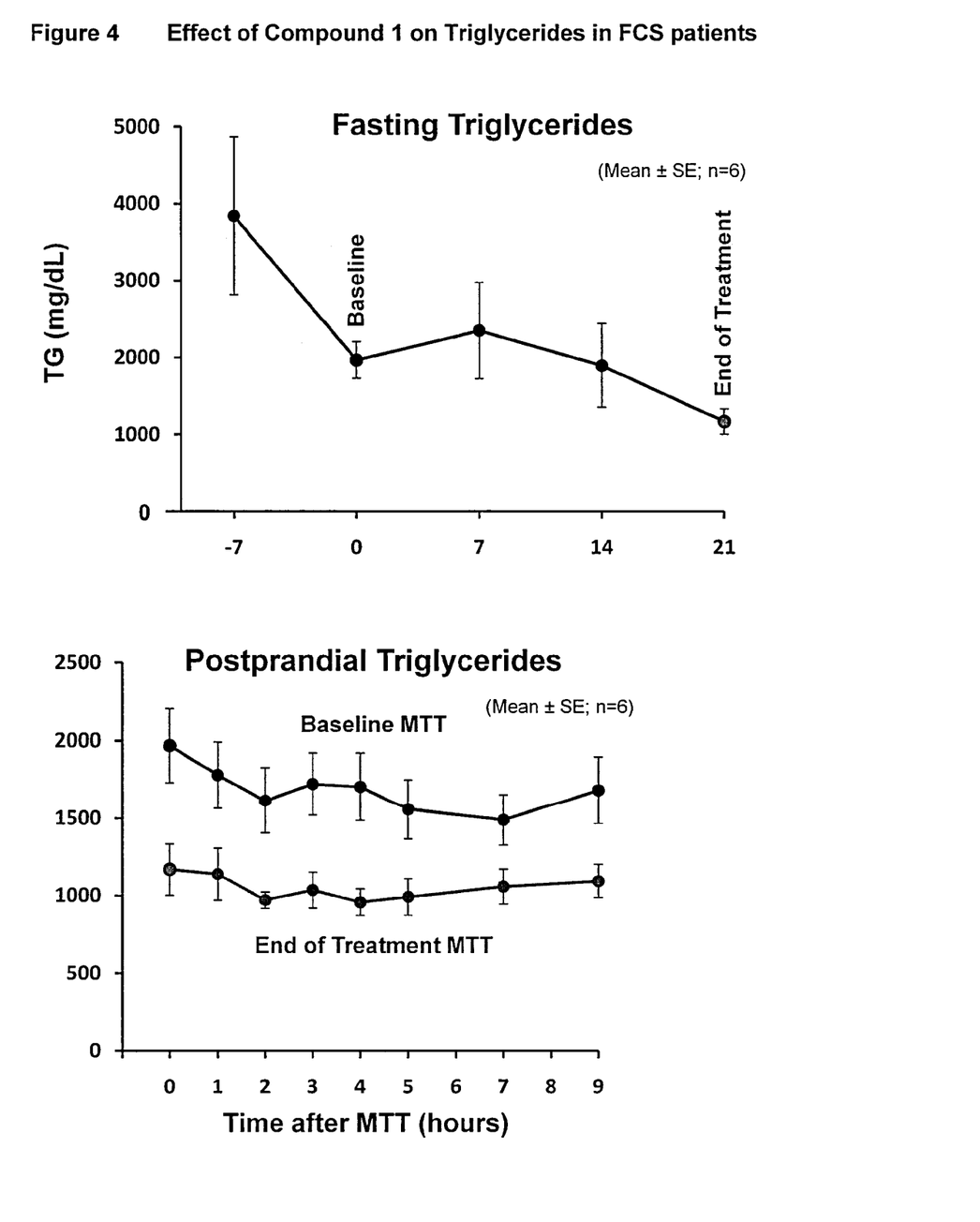
FIG. 4 shows the effect of the specific DGAT inhibitor designated as Compound 1 on triglycerides in FCS patients.

Fasting triglycerides were decreased by 38.4% in patients with FCS (FIG. 4 and Table 1). Furthermore, postprandial triglycerides were reduced by a similar magnitude in these patients. Triglyceride levels were thus decreased by about 40% to near the threshold for increased pancreatitis risk (about 1000 mg/dL).

TABLE 2

Effect of Compound 1 on Triglycerides in Type V patients

| Parameter for Type V patients (n = 6) | Mean Baseline | Mean Δ from Baseline |
|---|---|---|
| Fasting TG | 745.8 mg/dL | −23.6% |
| Postprandial Peak TG | 835.2 mg/dL | −25.8% |
| Postprandial TG $AUC_{0-9}$ | 6873.0 mg * h/dL | −27.3% | mg * h/dL = mg hour/dL

Figure 5:
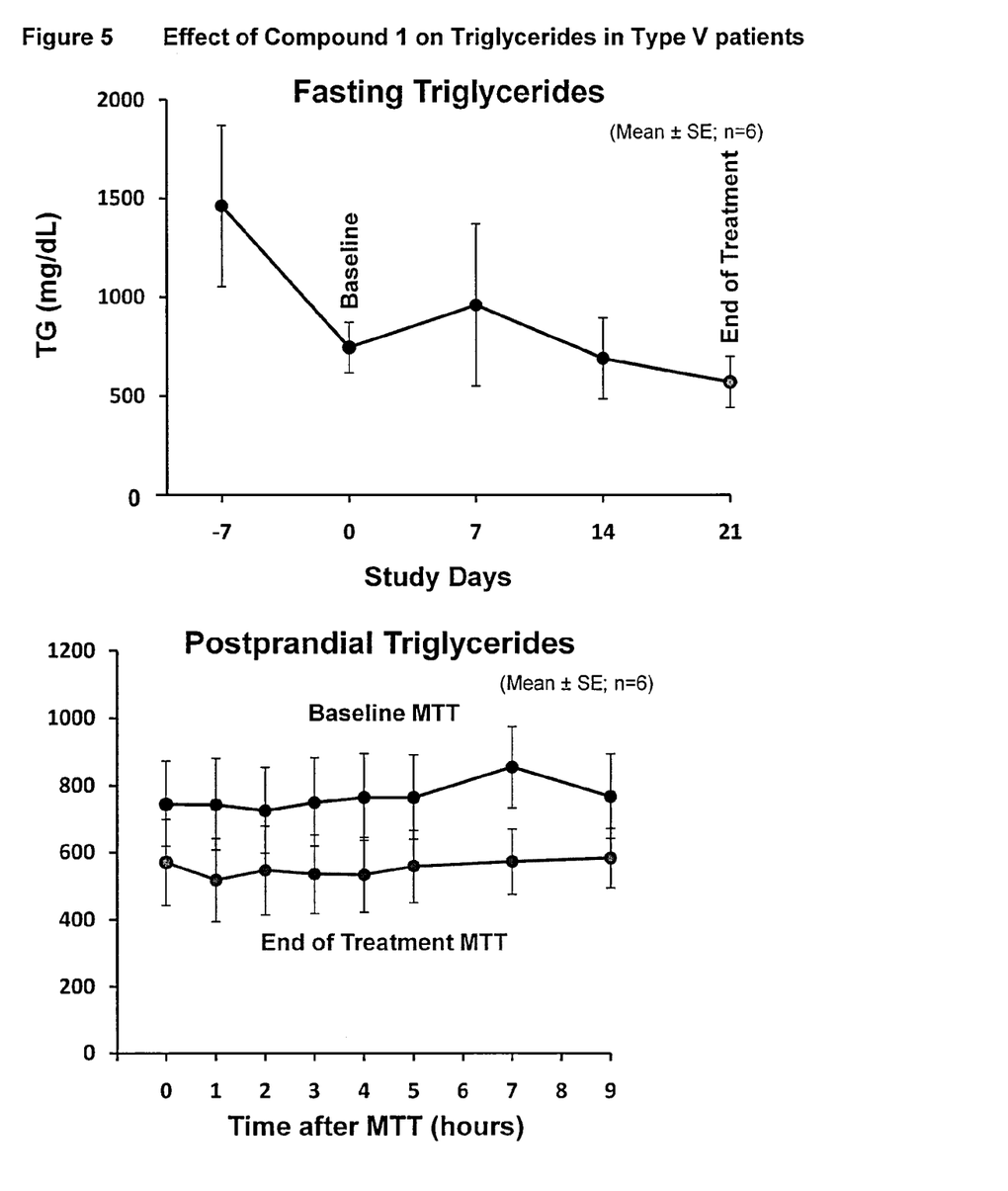
FIG. 5 shows the effect of the specific DGAT inhibitor designated as Compound 1 on triglycerides in Type V patients.

Triglyceride levels were decreased and kept well below the threshold for increased pancreatitis risk (about 1000 mg/dL). Thus, fasting triglycerides were decreased by 23.6% in Type V patients (FIG. 5 and Table 2). Furthermore, postprandial triglycerides were reduced by a similar magnitude in these patients.

The invention claimed is:

1. A method for the delay of progression or treatment of chylomicronemia due to familial chylomicronemia syndrome comprising administration of a therapeutically effective amount of the DGAT1 inhibitor trans-4-[4-[5-[[6-(trifluoromethyl)-3-pyridinyl]amino]-2-pyridinyl]phenyl]cyclohexane acetic acid, or a pharmaceutically acceptable salt or ester thereof, to a human subject in need of such treatment.

2. The method of claim 1 wherein the administration of the DGAT1 inhibitor reduces postprandial triglyceride levels in the subject.

3. The method of claim 1 wherein the administration of the DGAT1 inhibitor treats or delays the progression of a symptom selected from recurrent episodes of deposition of triglycerides in the skin in the form of eruptive xanthomas, hepatosplenomegaly, milky white triglyceride in the blood vessels in the back of the eye (lipemia retinalis), and mild neuro-cognitive deficits due to familial chylomicronemia syndrome.

4. A method according to claim 1 wherein the DGAT1 inhibitor is trans-4-[4-[5-[[6-(trifluoromethyl)-3-pyridinyl]amino]-2-pyridinyl]phenyl]cyclohexane acetic acid, sodium salt:

5. A method according to claim 4 wherein the DGAT1 inhibitor is used at a dose of 5-40 mg.

* * * * *